United States Patent [19]

Kissel et al.

[11] Patent Number: 5,081,314
[45] Date of Patent: Jan. 14, 1992

[54] PROCESS FOR PRODUCING ACROLEIN

[76] Inventors: Charles L. Kissel, 2856 W. Skywood Cir., Anaheim, Calif. 92804; Charles M. Finley, 300 W. Lemon Ave., Arcadia, Calif. 91007

[21] Appl. No.: 623,595

[22] Filed: Dec. 7, 1990

[51] Int. Cl.$^5$ .................. C07C 45/35; C07C 47/21
[52] U.S. Cl. .................. 568/479; 568/470; 568/476; 568/481
[58] Field of Search ............ 568/471, 472, 474, 470, 568/449, 485, 476, 479

[56] References Cited

U.S. PATENT DOCUMENTS

| | | | |
|---|---|---|---|
| 3,423,329 | 1/1969 | Gruber | 568/479 |
| 3,655,750 | 4/1972 | Ondrey et al. | 568/479 |
| 3,879,453 | 4/1975 | Ono et al. | 260/533 N |
| 3,936,505 | 2/1976 | Oda et al. | 568/479 |
| 4,025,565 | 3/1977 | Oda et al. | 568/479 |
| 4,029,636 | 6/1977 | Lowry et al. | 568/479 |
| 4,148,757 | 4/1979 | Brazdil et al. | 252/432 |
| 4,298,763 | 11/1981 | Engelbach et al. | 568/479 |
| 4,618,593 | 10/1986 | Sasaki et al. | 502/20 |

FOREIGN PATENT DOCUMENTS

| | | | |
|---|---|---|---|
| 1447982 | 6/1966 | France | 568/479 |
| 963610 | 7/1964 | United Kingdom | 568/479 |
| 1146870 | 3/1969 | United Kingdom . | |
| 2054569 | 2/1981 | United Kingdom . | |

OTHER PUBLICATIONS

G. W. Keulks, et al., "The Catalytic Oxidation of Propylene," *Journal of Catalysis*, vol. 34, pp. 79-97 (1974).
Derwent Abstract 47787B/26 to Japanese Patent Document 54-061,111.
Derwent Abstract 83-774714/39 to Netherlands Patent Document 8200521.

*Primary Examiner*—Werren B. Lone
*Attorney, Agent, or Firm*—Rosenblatt & Associates

[57] ABSTRACT

Dilute solutions of acrolein are produced on site and on demand by oxidizing propylene in an improved reactor using an improved catalyst, which is a mixture of molybdenum, bismuth and tellurium oxides. The catalyst is deposited on metal particles, which are of a metal selected from the group consisting of aluminum, tantalum, titanium, tungsten, niobium and mixtures thereof, and are packed to form a catalyst bed which provides improved heat transfer and distribution for better control of the process. The reaction is conducted in a reactor in which all the exposed surfaces are made of a metal selected from the group just mentioned. The produced acrolein is absorbed to form a dilute solution of acrolein in a liquid to be treated, such as irrigation water for weed control, or control of hydrogen sulfide in water used for oil and gas field water floods, or in fuel oil to inhibit growth of organisms.

25 Claims, 5 Drawing Sheets

PROCESS FOR PRODUCING ACROLEIN

FIELD OF THE INVENTION

The invention relates to methods for producing acrolein, and more particularly, the invention relates, in one aspect, to methods for making acrolein which employ a catalyst and even more particularly to catalytic methods for synthesizing acrolein in chemical reactors which may be portable.

BACKGROUND OF THE INVENTION

For many years, acrolein ($C_3H_4O$) has been produced by controlled oxidation of propylene ($C_3H_6$) in the presence of suitable catalysts. Examples of such catalysts and methods for making them are disclosed in British Patents Nos. 963,610 and 1,146,870; French Patent No. 1,447,982; and in the Japanese reference C. Z. Xing and H. Inoue, *Kagaku Kogaku Ronbunshu*, Vol. 10, No. 4, pp. 439-45 (1984).

Acrolein has many important uses, including treatment of waste water or water used to pressurize oil and gas fields, where the addition of only 6-10 parts per million (ppm) of acrolein controls the growth of microbes in feedlines to prevent plugging. Acrolein also scavenges hydrogen sulfide ($H_2S$) from aqueous solutions to reduce corrosion. Acrolein can also be used to make other products, e.g., glycerine, allyl alcohol, glycidol, glutaraldehyde, and propanol.

The biological activity of acrolein also prevents growth of organisms in liquid fuels, such as jet fuel, and controls the growth of algae, aquatic weeds, mollusks, and the like, in irrigation and process water systems. Slime formation is a serious problem in paper manufacturing, but is controlled by the use of only 0.4-0.6 ppm acrolein as a slimicide.

Acrolein has been made commercially for more than 40 years by the catalytic air oxidation of propylene using large fixed-bed reactors and fluidized bed reactors which require large manufacturing sites and high capital expenditures. The resulting crude acrolein undergoes expensive purification, which results in commercial grade (96%) acrolein. This concentrated acrolein is then packaged, transported, repackaged, and distributed to the end-user's facility. The concentrated acrolein is usually stored for long periods (often several months to a few years) before it is actually used. This procedure increases the possibility of accidental spills and premature reaction due to excessive handling, transportation and storage.

In prior art procedures using acrolein to treat irrigation or process water, liquid fuel, or the like, the commercial grade acrolein is purchased in bulk, and thereafter added to the liquid to be treated in an amount to give the desired concentration of acrolein. Properly performed, this procedure usually gives good results, but it is subject to the inherent hazards arising from the instability of concentrated acrolein. In the absence of a suitable inhibitor, acrolein rapidly polymerizes in the presence of light or heat to form a highly crosslinked solid of little or no use. Accordingly, concentrated acrolein requires an inhibitor, such as hydroquinone, to prevent that reaction.

Even though appropriate procedures for handling concentrated acrolein are well known, unwanted reactions occur, resulting not only in the loss of the acrolein, but sometimes the storage and handling equipment as well.

The hazards of handling, shipping, and storing concentrated acrolein could be reduced by diluting it, say, with water. However, storage of dilute acrolein usually results in the degradation of the material over time. In the case of water, hydrolysis ensues, producing hydrolysis products that have little or no biocidal or hydrogen sulfide scavenging performance. Maximum levels of acrolein dissolved in water are about 19-25%, depending on temperature. After a few days, these levels diminish to only a few percent. U.S. Pat. Nos. 4,215,147 and 4,215,148 describe the use of systems at low pH to extend the life of acrolein in water. Unfortunately, after several weeks to a few months, the level of acrolein decreases to low, unusable levels.

Because of its hazardous nature, acrolein is not generally used in offshore oil production platforms. Furthermore, increasing concerns of accidents during transportation on public highways and use in areas of high-density populations significantly retard the use of acrolein, and are beginning to reduce its usage, because a chemical accident could cause disastrous consequences.

SUMMARY OF THE INVENTION

This invention overcomes the problems arising from handling concentrated acrolein, and provides a portable, self-contained system for generating a dilute solution of acrolein in significant quantities on-demand and on-site. With the system of this invention, the acrolein is not produced and shipped in a concentrated liquid form, but instead is produced and used in a relatively short time on site in a dilute solution in a liquid compatible with the liquid to be treated.

Alternatively, the undiluted or only partially diluted acrolein can be used in well-known reactions to form other products, such as glycerine, allyl alcohol, glycidol, glutaraldehyde and propanol. If desired, the acrolein produced in accordance with this invention can be purified and used to make these, and other, products.

This invention also provides an improved catalyst and catalyst bed for generating acrolein in significant quantities in a portable, self-contained reactor by simply oxidizing propylene in the presence of air.

In carrying out these and other objects of the invention, there is provided, in one form, a method for producing acrolein comprising the steps of (1) injecting propylene and oxygen into a reactor; (2) reacting propylene and oxygen in the presence of a catalyst on a catalyst support to produce a reaction product containing acrolein, where the catalyst is a mixture of bismuth, molybdenum and tellurium oxides; and (3) removing the reaction product from the reactor.

The improved reactor of this invention can give a high yield to products from a reaction zone of about equal to or less than 18 inches long. Conventional prior art reactors are 10 to 30 times longer, making them impractical for use in portable units. While the reactor of this invention may be scaled up to produce greater volumes of product, even to the point that the reactor is no longer portable, such increase is expected to be accomplished by adding modules or cells, rather than appreciably increasing the size of the reactor chambers.

A presently preferred configuration of the reactor uses an air pump; a storage tank for the propylene; a pump for water or other liquid into which the acrolein is to be dissolved or absorbed; a high-temperature reactor thermally insulated and suitably shaped (for example, substantially in the form of a cube) for minimum consumption and loss of energy; an absorber system to collect product from the reactor and place it into a liquid at high efficiency; an exhaust gas purifier; and a control system using gauges, valves, sensors, and electrical circuits for positive, safe operation. The system can be sufficiently small to be mounted on a skid or a trailer, and only the reactants, the liquid and either electricity or fuel for an electrical generator are required to permit on-site and on-demand generation of acrolein dissolved in a flowing liquid stream. With this invention, there is no need to produce a concentrated liquid product, thus avoiding any inherent hazards that might be present with the product in that form. The system may also be sufficiently large so that it would be part of a permanent installation.

BRIEF DESCRIPTION OF THE DRAWINGS

These and other aspects of the invention will be more fully understood from the following detailed description taken in conjunction with the accompanying drawings, in which.

DETAILED DESCRIPTION OF THE INVENTION

Figure 1:
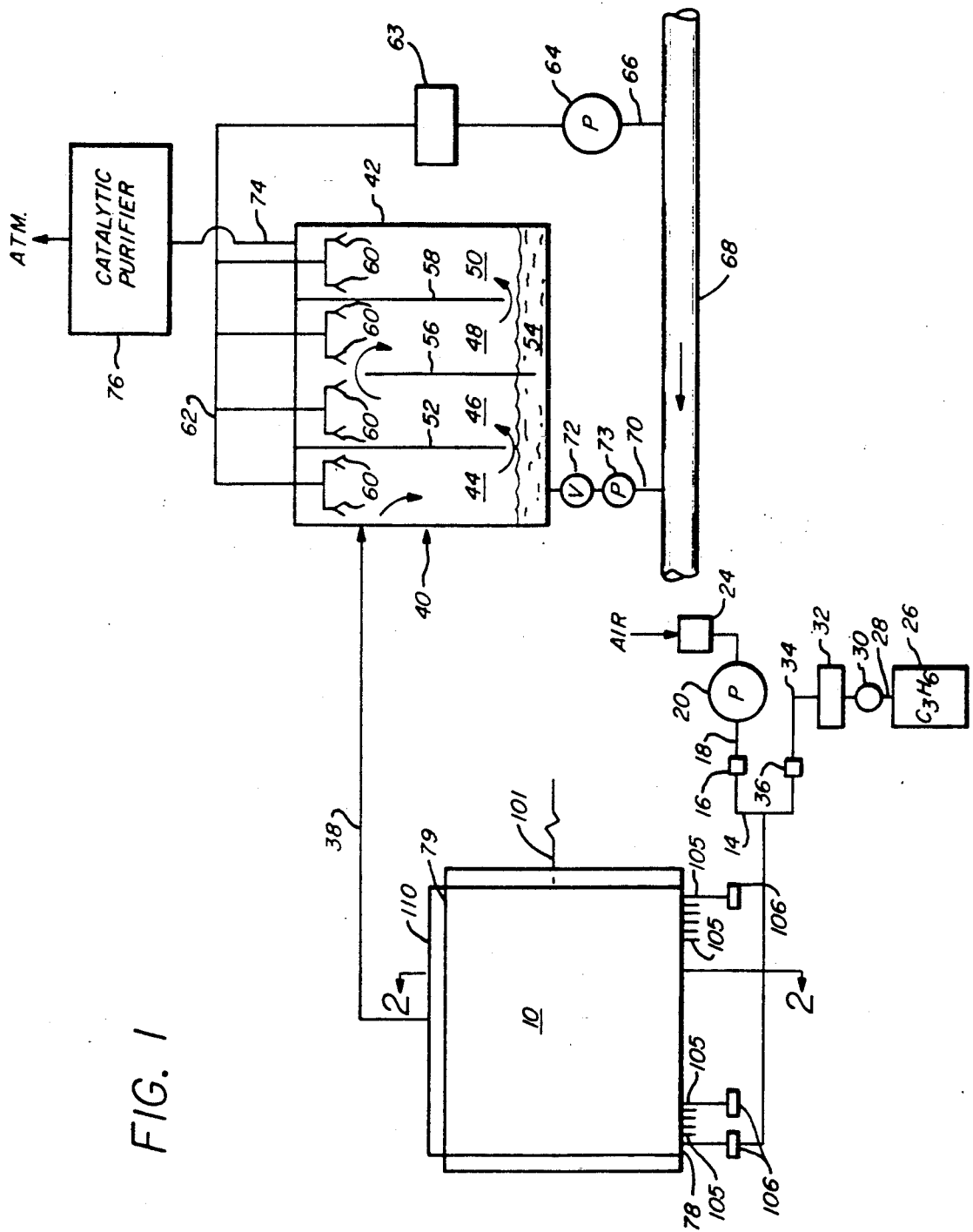
FIG. 1 schematically shows the reactor of this invention connected to receive a mixture of two gases, and to discharge the reaction products into an absorber.

It has been discovered that acrolein may be produced by reacting propylene and oxygen in a heated reaction zone in the presence of a catalyst that is the mixture of bismuth, molybdenum and tellurium oxides.

The apparatus capable of serving as the reactor can have various shapes, such as cylindrical or rectangular blocks, each containing hollow passageways capable of containing the catalyst and the reaction. These passageways may be tubular in nature, or they may be configured as to form a fixed-bed chamber, or numerous single tubes can be assembled in various arrays. Spouted beds or fluidized reactor zones could also be used. However, many of these reaction chamber types have inefficient temperature/heating characteristics, or serious channelling of unreacted starting material gases often occurs.

A preferred apparatus for making acrolein includes a reactor of this invention with at least one pair of substantially parallel plates disposed side-by-side. Each plate includes catalyst or reaction chambers which each have a respective inlet and outlet. A catalyst in each chamber promotes the oxidation reaction of propylene to acrolein, and a mechanism is provided for introducing the reactants, such as a mixture of propylene and oxygen, into the catalyst chambers through the inlets. A heating element or panel between the plates heats the reactants and the catalyst to a temperature which causes the reactants to react with each other in the presence of the catalyst to form the reaction products, which include acrolein. A mechanism is also provided for removing the reaction products from the outlets of the catalyst chambers.

In a preferred embodiment of the reactor, each plate is in the shape of a rectangular slab having major sides many times greater than the thickness of the slab. The slab has a first minor end and a second minor end opposite the first minor end. For example, each plate may be a rectangular slab about 1" thick, with opposing major faces each being approximately square and having a dimension of about 18" on each side. A plurality of elongated and laterally spaced bores extend through each plate in a direction substantially parallel to the major faces of the plate beginning at the first minor end and terminating at the second minor end, to provide as many as 20 to 30 parallel catalyst chambers in each plate. The reaction chambers may be said to extend from one minor end to an opposing minor end on opposite sides of the plate, beginning at one end with their inlet and terminating at the other with their outlet.

A thin, panel-shaped flat heating element is sandwiched between adjacent major faces of a pair of plates to form a heated pair, or cell, the temperature of which is controlled by a thermostat mounted in a face of one of the plates adjacent the heating element. Preferably, heat insulation around the assembled plates which form the reactor limits the amount of external energy which must be applied to the apparatus. A separate respective capillary tube is connected at one end to a respective catalyst or reaction chamber inlet, and at the other end to a reactant supply pipe, which supplies a mixture of reactants to each catalyst chamber inlet through a respective capillary tube. These capillary tubes are fed by a common header containing pressurized mixed starting materials. This arrangement uses frictional drag in the tubes to control the flow rates through each of the separate reaction chambers. Although capillaries are preferred for flow control, other devices, such as orifices or adjustable valves, may also be used.

A separate elongated collection header over the outlets of the catalyst chambers in each plate collects reaction products leaving the reaction chambers. Each of the catalyst chambers is packed with a bed of catalyst which preferentially promotes the reaction, such as the oxidation of propylene to acrolein.

The presently preferred embodiment of the invention includes a plurality of pairs of parallel plates, each pair being constructed and arranged with a panel-shaped heating element as described above. A sufficient number of the pairs of plates are staked together to form an array, or a reactor, essentially in the shape of a cube to minimize heat loss. In another embodiment, the plates could be curved or flat and arranged concentrically. The space between adjacent pairs of plates is thermally insulated to provide good temperature control in each pair of plates served by a respective panel-shaped heating element.

Preferably, the plates are made of a metal selected from the group of aluminum, tantalum, titanium, tungsten, niobium or mixtures thereof, or at least the inner surfaces of the reaction chambers are made from these metals. For example, a liner could be used as the inner surface of the chambers. The term "mixtures" as used herein includes alloys of the above-listed metals with each other, as well as other ways in which the various suitable metals may be mixed, such as simply being blended or clad together or used physically adjacent one another. It is additionally preferred that all internal surfaces contacted by the gases and/or liquids passing through the catalyst chambers and collection headers, absorber, if present, and conduits connecting the headers and absorbers or other pieces of equipment are made of metals selected from that group. It is possible that some tubing and conduits not subject to high temperatures may be made from inert polymeric plastics, elastomers and the like.

The preferred catalyst is a mixture of bismuth, molybdenum and tellurium oxides deposited on metal particles, such as spheres, shavings or the like, made of aluminum or other metal selected from the group of tantalum, titanium, tungsten, niobium or mixtures thereof. Again, the term "mixtures" includes alloys of these metals with each other, as well as other ways in which the various suitable metals may be mixed. Depositing the catalyst on the metal particles improves temperature control and significantly improves acrolein yield. Preferably the ratio of catalyst-to-metal particles on which the catalyst is deposited increases in the direction from the catalyst chamber inlet to the outlet. For example, the ratio of the catalyst-to-metal particles, by volume, may be about 1:3 in the first third of the catalyst chamber, about 1:2 in the middle third of the catalyst chamber, and about 1:1 in the last third of the catalyst chamber.

Preferably, the metal particles are spheres or granules the equivalent of spheres having a diameter in the range of about 0.02 to 5.0 mm. The cross-sectional area of each chamber is between 0.70 and 3.0 cm$^2$, and preferably is in the range of about 1.2 to 1.7 cm$^2$. Thus, the ratio of the diameter of the reaction chamber to the diameter of the catalyst support ranges from about 2:1 to about 200:1 and more preferably from about 5:1 to about 20:1.

Suitable mechanisms are provided for sensing the temperature of the catalyst and controlling the heat supplied by the heaters to keep the catalyst temperature within its operating range between about 300° to about 460° C., preferably at about 410° C.

A preferred form of the apparatus for the method of the invention also includes a pump for taking a stream of liquid from a source of liquid which is to be treated with the reaction product. Spray nozzles connected to the pump outlet, or other source of liquid under pressure, spray liquid into an absorber, through which the reaction products from the catalyst chambers pass. The reaction product is absorbed in the liquid stream from the liquid supply, and added to the system which is to be treated, either as a stream diluted by the system to be treated, or undiluted if the system to be treated is composed wholly of the product stream from the reactor. If gases are a product, those which are not absorbed in the liquid sprayed into the absorber pass through a catalytic purifier.

The method of this invention will now be described in even more detail for further illustration.

THE SYSTEM

Referring to FIG. 1, a reactor 10 in the general shape of a cube receives a gas mixture of air, as one reactant, and propylene, as the other reactant, from a plurality of horizontal and parallel supply lines 12 (see FIG. 2), each connected at respective inlet ends through a respective T-joint 14 to the discharge of a respective air pressure regulator 16, the inlet of which is connected by an air manifold line 18 to the discharge of air pump 20 having an inlet 22 connected to a filter 24, through which air is drawn.

A tank of one of propylene has a discharge line 28 connected through a primary pressure regulator 30 and a filter 32 to a gas supply line 34 connected through a secondary pressure regulator 36 to the T-joint 14.

Reaction products from the upper side of the reactor are carried by a delivery pipe 38 (see FIG. 1) to an absorber 40, which includes a housing 42 divided into first, second, third and fourth absorption zones 44, 46, 48 and 50, respectively. A first vertical baffle 52 extends from the top of the housing 42 downwardly to terminate just above a pool 54 of liquid, which may be water, fuel, or other liquid which absorbs acrolein. A second vertical baffle 56 mounted in the housing parallel to, and spaced horizontally from, the first baffle extends from below the level of liquid pool 54 and a short distance below the top of the housing. A third vertical baffle 58 parallel to, and spaced from, the second baffle extends from the top of the housing down to terminate just above the surface of the liquid pool 54. Each of the baffles extends entirely across the housing in a direction perpendicular to the plane of FIG. 1 so that the three baffles divide the housing 42 into the four absorption zones 44, 46, 48 and 50.

A separate respective group of spray nozzles 60 mounted in the upper end of each absorption zone are supplied liquid from a liquid supply pipe 62 connected through a pressure regulator 63 to the discharge of a pump 64, which has as its inlet connected through a suction pipe 66 to a main body or stream of liquid flowing through a main pipe 68. Line 66 and pump 64 may be replaced by other suitable sources, such as pressurized water lines typical of fire hydrants and hose bib stand pipes. In any event, the pressure of the incoming fluid is determined by a pressure regulator 63, or other suitable flow-monitoring device.

A drain pipe 70 extends from the liquid pool 54 in the housing through a control valve 72 and a return pump 73 to return acrolein-containing liquid in the absorber to the main pipe 68. Alternatively, the acrolein-containing liquid may be sent to storage for future use.

An exhaust conduit 74 carries unabsorbed gases from the upper end of the fourth absorption zone 50 to a catalytic purifier 76, which oxidizes the remaining hydrocarbons and any carbon monoxide to water and carbon dioxide, which are discharged to the atmosphere.

THE REACTOR

Figure 2:
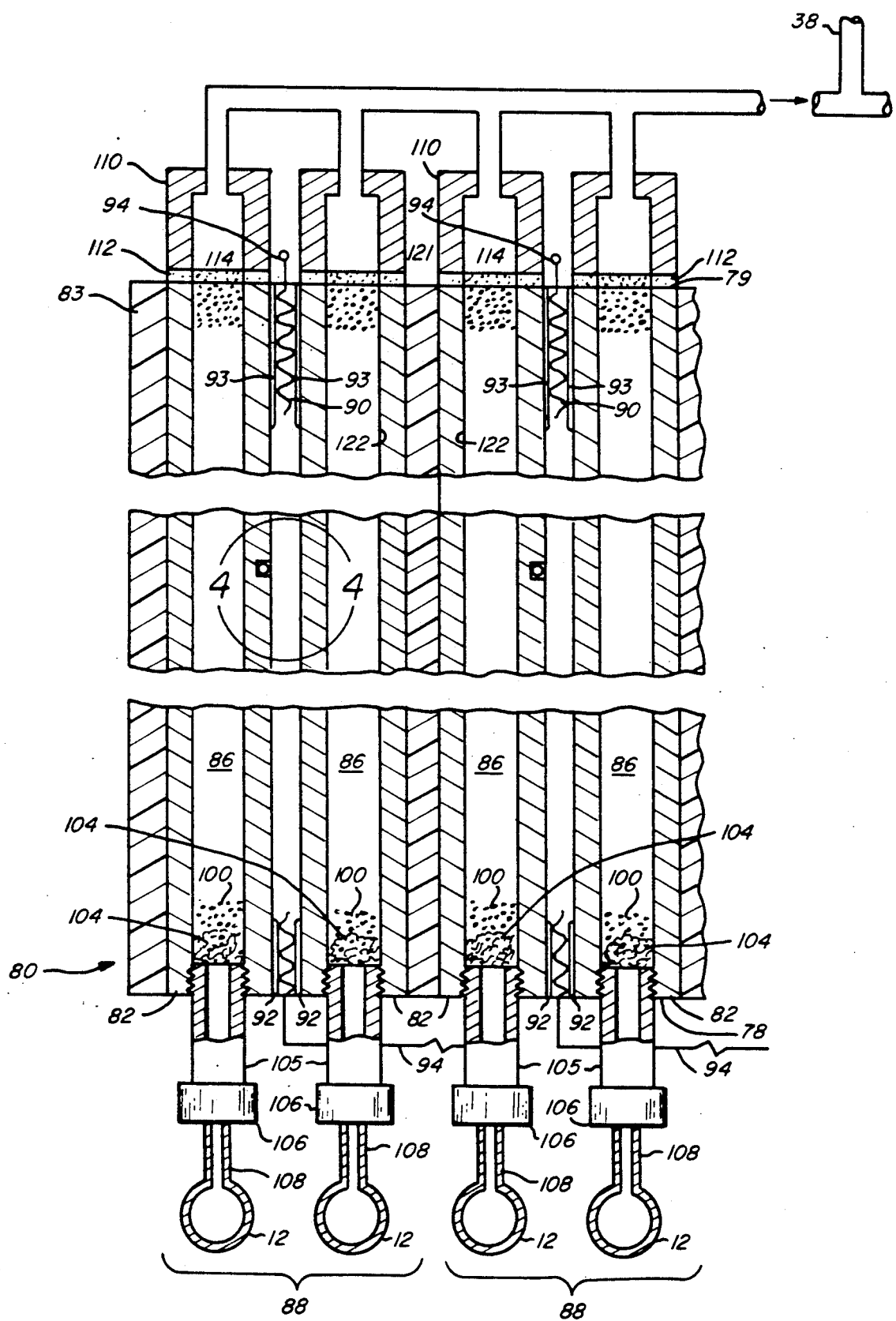
FIG. 2 is a view taken on line 2—2 of FIG. 1 showing details of the reactor in cross-section.
Figure 3:
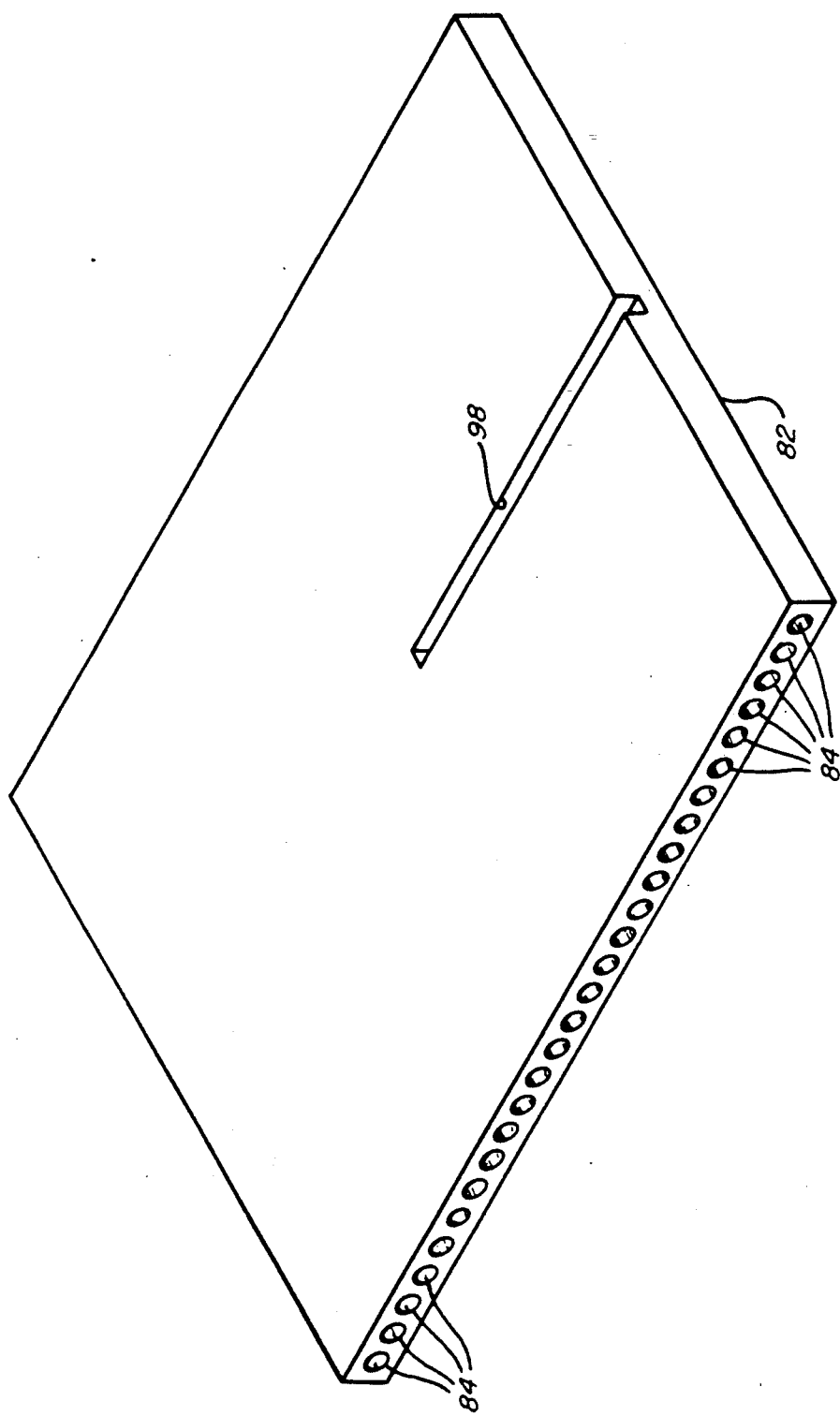
FIG. 3 is a perspective view of one of the parallel plates in the reactor.

As shown in FIG. 2, the reactor 10 may be a sandwich assembly or array 80 of a plurality of flat, rectangular plates or slabs 82 disposed side-by-side so the reactor is substantially in the shape of a cube to minimize heat loss from a given volume for the reactor. A layer 83 of thermal insulating material surrounds the reactor to reduce heat loss and energy consumption. Each plate 82 has a first minor end 78 containing the inlets to the reactor plate, and a second minor end 79 opposite the first minor end containing the outlets. First minor end 78 and second minor end 79 are generally perpendicular to the major face of slab 82.

Although the plates may be of any suitable dimensions, a successful reactor has been designed in which the plates are about 18"×18"×1". The plates are assembled with their major surfaces vertically oriented to form the assembly 80 shown in FIG. 2. A plurality of vertical bores 84 extend through each plate. If the plate is about 1" thick, it has been found that bores about ⅛" in diameter, and located on about ⅜" centers form properly spaced and dimensioned reaction chambers 86 (FIG. 2).

Figure 5:
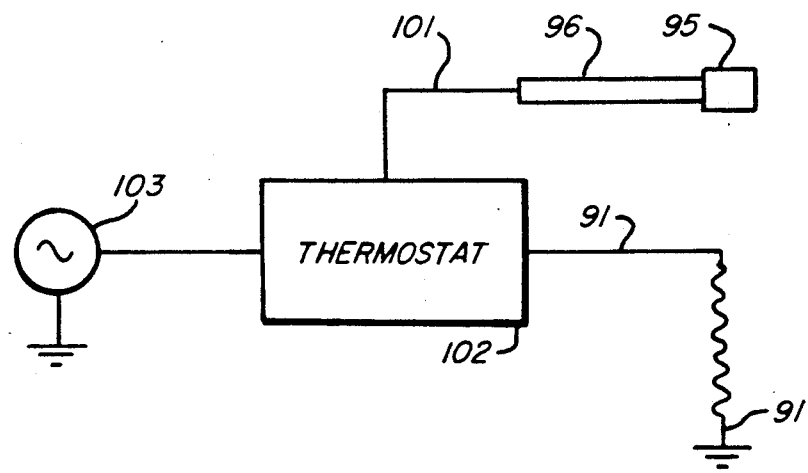
FIG. 5 is a schematic diagram showing a circuit for controlling the temperature of the catalyst in the reactor.

The plates may be arranged in pairs 88 (FIG. 2), with a separate, respective, flat electrical heating panel 90 disposed between adjacent faces 92 of each plate in each pair. A pair of plates with a heating panel 90 between them may be referred to as a cell or module. A thin, separate, respective sheet 93 of ceramic insulation is between each face of each electric panel and the adjacent face of a plate. The thin sheet of ceramic insulation, which can be of any suitable thickness, say 0.03 to 0.07", provides a more uniform transfer of heat from the electric heating panels 90 to the entire adjacent surfaces of the plates. Electrical power leads 94 (FIGS. 2 and 5) supply power to the heater panels. Alternatively, the reactor could consist of one plate 82 and one adjacent flat electrical heating panel 90.

Figure 4:
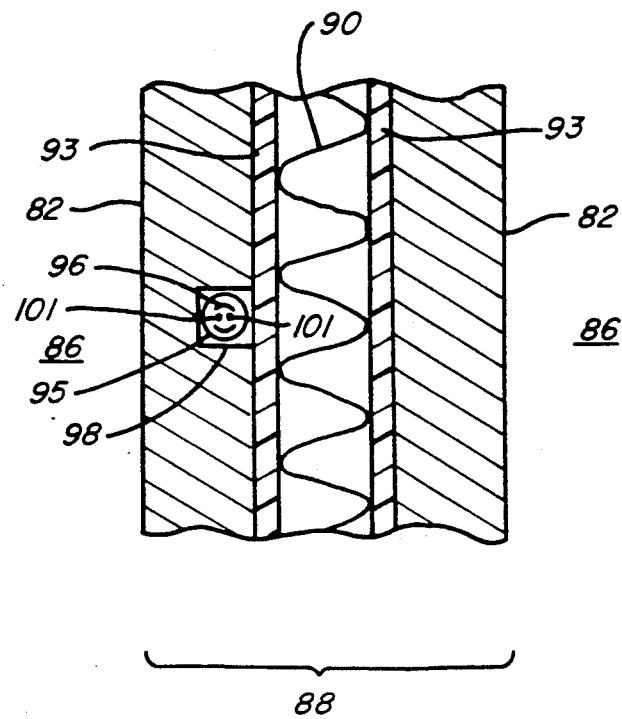
FIG. 4 is an enlarged view taken in the area 4—4 of FIG. 2.

A thermocouple 95 on the inner end of a horizontal support 96 (FIGS. 4 and 5) in a horizontal groove 98 extending from about the center of one vertical edge of a plate in each pair to about the center of that plate, and opening toward the other plate in the pair, senses the temperature of the plates surrounding the respective reaction chambers 86, each of which is filled with a bed 100 of a catalyst which promotes the oxidation of propylene to form acrolein. A separate pair of electrical signal leads 101 (see FIGS. 4 and 5) extend from each respective thermocouple to a respective adjustable thermostat 102, which controls the amount of electrical power supplied from a generator 103 to a respective electrical heater panel 90 to keep the catalyst in the adjacent reaction chamber 86 at the required operating temperature.

A separate, respective loose plug 104 (FIG. 2) of quartz wool in the bottom of each reaction chamber 86 rests on the upper end of a separate, respective short nipple 105 threaded into the lower end of a respective reaction chamber to form a reaction chamber inlet. The upper end of a separate, respective capillary tube 108 is sealed at its lower end to a respective gas supply pipe 12. The capillary tubes act as flow control devices and may be of any suitable internal diameter for that purpose. Capillary tubes with an inside diameter of about 0.007" provide good flow control and distribution of reactant gas from the supply pipes 12.

A separate, elongated, rectangular header 110 rests on a separate, respective graphite gasket 112 on the upper edge of each plate and over the upper (outlet) ends of the reaction chamber in each plate to collect reaction products which flow up through the reaction chambers, through respective holes 114 in the gaskets 112, and to the delivery pipe 38 (see FIGS. 1 and 2).

The reactor plates and all other components with surfaces contacted by the reaction products should be made of a material which has good thermal conductivity, and which does not adversely affect the production of the desired product. For example, to produce acrolein by oxidizing propylene, aluminum is preferred because of its relatively low cost. Other metals, such as tantalum, titanium, tungsten, niobium or mixtures of these, may also be used. Again, mixtures may encompass blends, clads or alloys. Aluminum alloys of the 6000-type are preferred because they are inert, machinable, and can be welded. These are unusual materials for reactors, but have been found to be particularly advantageous for catalytic oxidation reactions, particularly the production of acrolein from propylene. The use of ferrous metals within the reactor decreases the selectivity of the process to acrolein. Brass, bronze and copper are also not used because they deteriorate chemically when contacted with such reactants as air and propylene. We are not aware of any prior art use of aluminum equipment, except for the single report of the use of aluminum tubes that were coated with copper as a catalyst described by Xing and Inoue, *Kagaku Kogaku Ronbunshu*, Vol. 10, No. 4, p. 439–45 (1984).

A separate respective panel 121 of thermal insulation between the adjacent outer faces 122 of each adjacent pair of plates provides good temperature control for each pair of plates served by a respective heating panel 90. The panels may be of any suitable material, such as sandstone, refractory material, spun glass, and the like. Each panel has sufficient thickness to reduce thermal flow between reactor pairs 88. Although asbestos, asbestos-filled materials such as magnesia, and transite can provide adequate protection against thermal convention, their use is discouraged due to possible environmental health hazards.

THE CATALYST

The preferred catalyst of the invention is a mixture of bismuth, molybdenum and tellurium oxides supported on particles of metal, such as aluminum, tantalum, titanium, tungsten, niobium or mixtures thereof. Here, the term "mixture" simply refers to blends of the various catalyst components and does not refer to alloy or clad configurations. The catalyst was deposited in a uniform, adherent layer over aluminum particles typically having a diameter of 1-2 mm. In a broader embodiment, the catalyst support particles may range from 0.02 to 5.0 mm in diameter. The catalyst support may be spherical in shape, but may also take other shapes, such as irregular granules and other shapes or metal shavings. The ratio of the reaction chamber diameter to the catalyst support diameter may range from about 2:1 to about 200:1, and preferably from about 5:1 to about 20:1.

In loading each reaction chamber 86 of the reactor 10, preferably the lower third of each chamber is filled with the catalyst support (aluminum) and the catalyst, which is about 1 part catalyst to 3 parts aluminum, by volume. The middle third of each reaction chamber has about 1 part catalyst to 2 parts aluminum, by volume, and the upper and last third of each reaction chamber is filled with a mixture of about 50% catalyst and 50% aluminum, by volume. Thus, the ratio of catalyst to aluminum support particles increases in the direction away from the reactor chamber inlet to provide better control of the conversion of propylene to acrolein because dilution of the catalyst with aluminum particles (particularly in that part of the bed contacting gas which is high in both oxygen and unreacted propylene) reduces the rate of chemical reaction and, thus, the tendency to generate excessive local temperatures. Other metal particles can also be used as a catalyst support, as long as the metal has good thermal conductivity, and does not adversely affect the production of acrolein.

THE PROCESS

The operation of the reactor to produce acrolein will now be described. With the reactor packed with beds of supported catalyst, as described above and shown in FIG. 2, a mixture of air and propylene in a ratio of 84:16, respectively, by volume, was fed into the inlets of the reaction chambers, which were heated to about 410° C. The pressure in the reaction chambers was between about 2 and about 5 lbs./in.$^2$, and the flow rate per unit of cross-sectional area was about 100 ml/min./cm$^2$. The effluent from the reaction chambers 86 flowed through the aluminum headers and the aluminum delivery pipe 38, which were surrounded by a layer of insulation (not shown) to keep the gas in them at a temperature above about 60° C. to prevent premature condensation of acrolein, and into the upper end of the first absorption zone of the absorber. The effluent was contacted in the first absorber zone by a spray of water supplied by pump 64 to the spray nozzles. The intake of the pump was connected to main pipe 68 carrying a main stream of water to be treated with acrolein. Water droplets with absorbed acrolein fell into the pool 54 in the bottom of the absorber. Unabsorbed gases passed under the first baffle 52 and into the bottom of the second absorption zone following the arrows shown in FIG. 1, rising to meet more water droplets sprayed into the top of that zone. Additional acrolein was absorbed and carried to the pool in the bottom of the absorber. The unabsorbed gases continued over the top of the second baffle into the top of the third absorption zone for additional absorption of acrolein, and passed under the third baffle to flow up through the spray of water in the fourth absorption zone, and out the exhaust conduit 74 through the catalytic purifier 76, where any carbon monoxide and unreacted hydrocarbons were oxidized to carbon dioxide and water vapor, which were discharged into the atmosphere.

The water sprayed into the absorber scrubbed more than 99.9% of the acrolein from the reactor effluent, and carried it into the liquid pool in the bottom of the absorber, where the acrolein-rich water was removed through the drainpipe 70 and returned to the main stream of water downstream of the pump inlet.

In the example just described, the concentration of the acrolein in the water pool in the bottom of the absorber was about 0.2%, by weight, and it was returned to the main water stream at a rate to give a treated solution with between about 1 and about 15 ppm acrolein for weed control in ditches through which the treated water flowed. Approximately the same concentration would be used for treating injection wells for secondary recovery of oil, or maintenance of gas pressure in an underground formation. In either case, the reactive nature of the acrolein in the dilute solution causes the acrolein to substantially disappear within a few days.

The acrolein added to water for secondary recovery can scavenge hydrogen sulfide (H$_2$S) and destroy microbes (e.g., anaerobic bacteria which consume sulfur, say from calcium sulfate which may be available in the injection water or in the formation, and convert it to H$_2$S, a corrosive compound), which may be in either the treated water, or downhole, or both.

As noted, the water or other fluid supplied to the absorber may come from a pressurized source, in which case the pump is not required. The water to be treated can come from a source of irrigation water, or water to be injected into an underground formation, and either all of the water to be treated can be passed through the absorber, which would be operated to give the required final concentration of acrolein, or only a portion of the water may be passed through the absorber and then recombined with the rest of the water, as described above. It is possible to operate the absorber to produce a solution which contains up to about 25% acrolein by weight.

Dilution of the catalyst with the metal support particles, particularly in that part of the bed contacting gas high in oxygen and unreacted propylene, reduced the rate of chemical reaction in the lower third of the catalyst beds, and thus the tendency to generate excessive local temperatures, which would be detrimental to the formation of acrolein.

Figure 6:
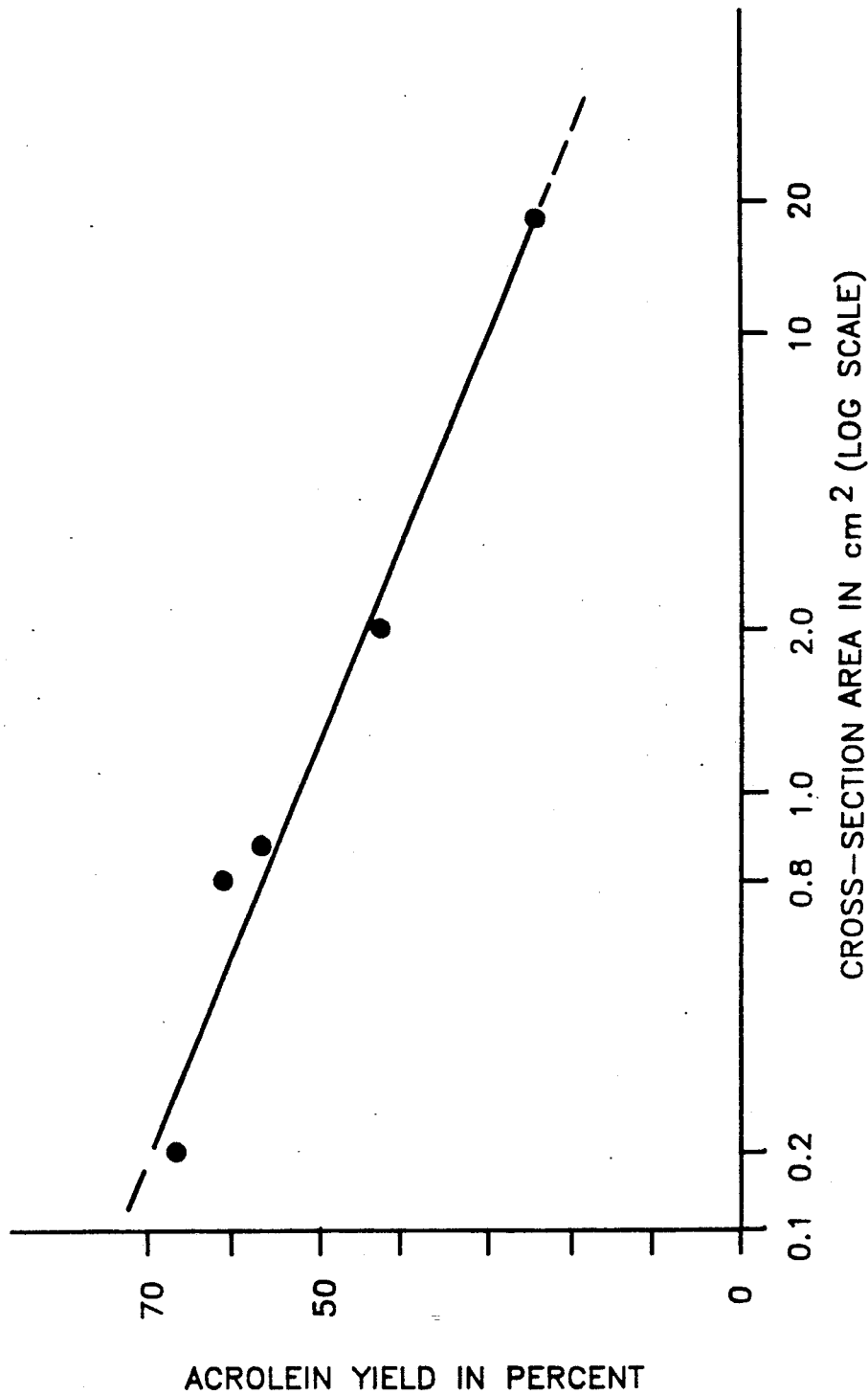
FIG. 6 is a diagram showing how acrolein yield decreases with increasing cross-sectional area of a reaction chamber.

It has been determined that in building a compact, portable reactor of the type described above, and in which a highly-divided catalyst is employed, it is advantageous in one embodiment to limit the cross-sectional area of each reaction chamber 86 to about 2 cm$^2$ or less, and to limit the flow rate of reactants to about 150 cc/min./cm$^2$ of cross-sectional area or less. FIG. 6 shows how acrolein yield varied as a function of cross-sectional area, at a flow rate of 110 cc of reactants per minute per cm$^2$ of cross-sectional area. Accordingly, to obtain a given throughput of reactants for a desired output of acrolein, a number of reaction chambers were grouped together, i.e. placed in parallel, as described above to permit accurate control of flow rate and temperature for each chamber. The number of parallel reaction chambers may be quite large to obtain a relatively large throughput of reactants and production of acrolein. The same result cannot be obtained by simply using a reactor with a large, undivided cross-sectional area equal to the total of the group of parallel reaction chambers. The yield of acrolein with the large, undivided cross sectional area is inevitably low and, therefore, uneconomic.

In operating the reactor of this invention as described above at 410° C., with a feed mixture of 16% propylene and 84% air, the discharge from the reactor was 9.4% acrolein, resulting in a yield of approximately 68% of the propylene to acrolein.

Many modifications may be made in the apparatus of the present invention without departing from its spirit and scope, which are defined only in the appended claims. For example, one skilled in the art may find that certain geometric configurations of the flat plates, or certain alloys of the preferred metals of the reactor materials or the catalyst support give particularly advantageous results. From the foregoing description, it will be seen that this invention provides a portable, self-contained system for generating acrolein on demand and on-site to produce dilute, safe solutions of acrolein, which has many uses, including control of corrosion in drilling for, or producing, oil or gas, or control of algae, weeds, mollusks, slime and the like in irrigation and process water systems. The acrolein can also be absorbed as needed in organic liquids, such as hydrocarbon fuel, to control the growth of microbes.

We claim:

1. A method for producing acrolein comprising the steps of:
    injecting propylene and oxygen into a reactor;
    reacting propylene and oxygen in the presence of a catalyst on a catalyst support to produce a reaction product containing acrolein, where the catalyst is a mixture of bismuth, molybdenum and tellurium oxides; and
    removing the reaction product from the reactor.

2. The method of claim 1 where the reactor comprises:
    at least one plate having
        a major surface;
        a first minor end;
        a second minor end opposite the first minor end;

a plurality of reaction chambers therein, parallel to one another and parallel to the major surface, beginning at the first minor end at an inlet and terminating at the second minor end at an outlet, the chambers for receiving a catalyst;

catalyst within the reaction chambers; and at least one heating panel adjacent and parallel to the flat plate.

3. The method of claim 2 where in the reactor at least an inner surface of the reaction chambers is selected from the group consisting of aluminum, tantalum, titanium, tungsten, niobium and mixtures thereof.

4. The method of claim 3 where the inner surface is aluminum.

5. The method of claim 2 where in the reactor the cross-sectional area of each reaction chamber is between 0.70 and 3.0 $cm^2$.

6. The method of claim 2 where the reactor further comprises means for introducing reactants through the inlets of the reaction chambers and means for removing a reaction product from the outlets of the reaction chambers.

7. The method of claim 2 where the ratio of catalyst to catalyst support, by volume, is about 1:3 in a first respective part of each reaction chamber, is about 1:2 in a second respective intermediate part of each catalyst chamber, and is about 1:1 in a third respective part of each catalyst chamber nearest the chamber outlet.

8. The method of claim 1 where the catalyst support comprises metal particles where the metal particles are selected from the group consisting of aluminum, tantalum, titanium, tungsten, niobium and mixtures thereof.

9. The method of claim 8 where in the catalyst support the metal particles have a rough diameter of from 1 to 2 mm.

10. The method of claim 8 where in the catalyst support the metal is aluminum.

11. The method of claim 8 where in the catalyst support, the catalyst is to be used in a tubular reactor of a first diameter and the catalyst support has a second diameter, and where the ratio of the first diameter to the second diameter ranges from 2:1 to 200:1.

12. The method of claim 1 where the reaction of propylene and oxygen is conducted at a temperature in the range of about 300° to 460° C.

13. A method for producing acrolein comprising the steps of:

injecting propylene and oxygen into a reactor;

reacting propylene and oxygen in the presence of a catalyst on a catalyst support to produce a reaction product containing acrolein, where the catalyst is a mixture of bismuth, molybdenum and tellurium oxides;

where the catalyst support comprises metal particles where the metal particles are selected from the group consisting of aluminum, tantalum, titanium, tungsten, niobium and mixtures thereof; and where the reaction of propylene and oxygen is conducted at a temperature in the range of about 300° to 460° C.; and removing the reaction product from the reactor.

14. The method of claim 13 where the reactor comprises:

at least one plate having
a major surface;
a first minor end;
a second minor end opposite the first minor end;
a plurality of reaction chambers therein, parallel to one another and parallel to the major surface, beginning at the first minor end at an inlet and terminating at the second minor end at an outlet, the chambers for receiving a catalyst, and where at least an inner surface of the reaction chambers is selected from the group consisting of aluminum, tantalum, titanium, tungsten, niobium and mixtures thereof;

catalyst within the reaction chambers; and at least one heating panel adjacent and parallel to the flat plate.

15. The method of claim 14 where in the reactor the cross-sectional area of each reaction chamber is between 0.70 and 3.0 $cm^2$.

16. The method of claim 14 where the reactor further comprises means for introducing reactants through the inlets of the reaction chambers and means for removing a reaction product from the outlets of the reaction chambers.

17. The method of claim 14 where the ratio of catalyst to catalyst support, by volume, is about 1:3 in a first respective part of each reaction chamber, is about 1:2 in a second respective intermediate part of each catalyst chamber, and is about 1:1 in a third respective part of each catalyst chamber nearest the chamber outlet.

18. The method of claim 13 where in the catalyst support the metal particles have a rough diameter of from 1 to 2 mm.

19. The method of claim 13 where in the catalyst support the metal is aluminum.

20. The method of claim 13 where in the catalyst support, the catalyst is to be used in a tubular reactor of a first diameter and the catalyst support has a second diameter, and where the ratio of the first diameter to the second diameter ranges from 2:1 to 200:1.

21. A method for producing acrolein comprising the steps of:

injecting propylene and oxygen into a reactor, where the reactor comprises:
at least one plate having
a major surface;
a first minor end;
a second minor end opposite the first minor end;
a plurality of reaction chambers therein, parallel to one another and parallel to the major surface, beginning at the first minor end at an inlet and terminating at the second minor end at an outlet, the chambers for receiving a catalyst, and
where at least an inner surface of the reaction chambers is selected from the group consisting of aluminum, tantalum, titanium, tungsten, niobium and mixtures thereof;
catalyst on a catalyst support within the reaction chambers;
where the catalyst is a mixture of bismuth, molybdenum and tellurium oxides; and
where the catalyst support comprises metal particles having a rough diameter of from 1 to 2 mm and where the metal particles are selected from the group consisting of aluminum, tantalum, titanium, tungsten, niobium and mixtures thereof; and;
at least one heating panel adjacent and parallel to the flat plate;

reacting propylene and oxygen in the presence of the catalyst to produce a reaction product containing acrolein, where the reaction of propylene and oxygen is conducted at a temperature in the range of about 300° to 460° C.; and removing the reaction product from the reactor.

22. The method of claim 21 where in the reactor the cross-sectional area of each reaction chamber is between 0.70 and 3.0 cm$^2$, and the reaction chambers are about 18" long and where the number of reaction chambers in each plate ranges from 20 to 30.

23. The method of claim 21 where the ratio of catalyst to catalyst support, by volume, is about 1:3 in a first respective part of each reaction chamber, is about 1:2 in a second respective intermediate part of each catalyst chamber, and is about 1:1 in a third respective part of each catalyst chamber nearest the chamber outlet.

24. The method of claim 21 where in the catalyst support and the inner surface of the reaction chambers, the metal is aluminum.

25. The method of claim 21 where in the catalyst support, the catalyst is to be used in a tubular reactor of a first diameter and the catalyst support has a second diameter, and where the ratio of the first diameter to the second diameter ranges from 2:1 to 200:1.

* * * * *